(12) United States Patent
Borges et al.

(10) Patent No.: US 12,036,383 B2
(45) Date of Patent: *Jul. 16, 2024

(54) ADJUSTMENT OF INFUSION USER INTERFACE UPON DOCKING EVENT

(71) Applicant: CareFusion 303, Inc., San Diego, CA (US)

(72) Inventors: Gregory Borges, San Diego, CA (US); Donald Halbert, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 171 days.

This patent is subject to a terminal disclaimer.

(21) Appl. No.: 17/244,356

(22) Filed: Apr. 29, 2021

(65) Prior Publication Data

US 2022/0008647 A1 Jan. 13, 2022

Related U.S. Application Data

(63) Continuation of application No. 15/405,760, filed on Jan. 13, 2017, now Pat. No. 11,013,853, which is a
(Continued)

(51) Int. Cl.
*A61M 5/14* (2006.01)
*A61M 5/142* (2006.01)
(Continued)

(52) U.S. Cl.
CPC ........ *A61M 5/1413* (2013.01); *A61M 5/1407* (2013.01); *A61M 5/142* (2013.01); *G16H 20/17* (2018.01); *G16H 40/63* (2018.01); *A61M 2005/14208* (2013.01); *A61M 2205/18* (2013.01); *A61M 2205/3561* (2013.01); *A61M 2205/3584* (2013.01); *A61M 2205/3592* (2013.01); *A61M 2205/50* (2013.01); *A61M 2205/505* (2013.01); *A61M 2205/52* (2013.01); *A61M 2205/581* (2013.01); *A61M 2205/582* (2013.01); *A61M 2205/583* (2013.01); *A61M 2205/6072* (2013.01);
(Continued)

(58) Field of Classification Search
CPC ................ A61M 5/1413; A61M 5/142; A61M 2005/14208; A61M 2205/18; A61M 2205/3561; A61M 2205/3584; A61M 2205/3592; A61M 2205/50; A61M 2205/505; A61M 2205/52; A61M 2205/581; A61M 2205/582; A61M 2205/583; A61M 2205/6072; A61M 2205/8206; A61M 2209/084; A61M 2209/086; G16H 20/17; G16H 40/63
See application file for complete search history.

(56) References Cited

U.S. PATENT DOCUMENTS 5,429,602 A 7/1995 Hauser
5,630,710 A 5/1997 Tune et al.
(Continued)

*Primary Examiner* — Wissam Rashid
(74) *Attorney, Agent, or Firm* — Mintz Levin Cohn Ferris Glovsky and Popeo, P.C.

(57) ABSTRACT

A patient care system includes a control unit capable of coupling with multiple modular medical devices. A modular medical device can be coupled with the control unit, wherein the behavior of the modular medical device automatically adjusts based on the status of being coupled or un-coupled with the control unit.

22 Claims, 3 Drawing Sheets

Related U.S. Application Data continuation of application No. 14/175,846, filed on Feb. 7, 2014, now Pat. No. 9,545,475.

(51) Int. Cl.
  *G16H 20/17* (2018.01)
  *G16H 40/63* (2018.01)

(52) U.S. Cl.
  CPC .............. *A61M 2205/8206* (2013.01); *A61M 2209/084* (2013.01); *A61M 2209/086* (2013.01)

(56) References Cited

U.S. PATENT DOCUMENTS

| | | |
|---|---|---|
| 6,593,528 B2 | 7/2003 | Franklin-Lees et al. |
| 8,255,585 B2 | 8/2012 | Levin |
| 8,312,877 B2 | 11/2012 | Elaz et al. |
| 9,132,234 B2 | 9/2015 | Estes et al. |
| 2005/0022274 A1 | 1/2005 | Campbell et al. |
| 2006/0229557 A1* | 10/2006 | Fathallah ............... G16H 40/63 705/2 |
| 2007/0060869 A1* | 3/2007 | Tolle ................. A61M 5/14244 600/300 |
| 2007/0088249 A1 | 4/2007 | Duffy et al. |
| 2009/0005729 A1 | 1/2009 | Hendrixson et al. |
| 2011/0119612 A1 | 5/2011 | Gannon et al. |

\* cited by examiner

ADJUSTMENT OF INFUSION USER INTERFACE UPON DOCKING EVENT

CROSS-REFERENCE TO RELATED APPLICATIONS

This application is a continuation of U.S. patent application Ser. No. 15/405,760 filed on Jan. 13, 2017, now U.S. patent Ser. No. 11/013,853, which is a continuation of U.S. patent application Ser. No. 14/175,846 filed on Feb. 7, 2014, now U.S. Pat. No. 9,545,475. The disclosures of which are hereby incorporated herein by reference in its entirety.

BACKGROUND

Infusion pump and sensing device systems are widely used in the medical field for infusing a fluid, such as a medication, to a patient in the environment of intensive care units, cardiac care units, operating rooms or trauma centers. Several types of infusion pump systems permit the infusion of several medications using pumps that are modularly coupled to one another, as it may often be necessary to simultaneously infuse into the patient several different kinds of fluids. Some of the several types of fluids, such as drugs, may not be directly compatible with each other and therefore need to be infused into the patient at different points of the body or at different times.

In this regard, there exist modular systems in which a pump module can be selectively attached, both physically and electrically, to a control unit.

SUMMARY

The control unit controls the operation of one or more pump modules attached to it. The control unit and the pump module may both include an integral or attachable display unit that is configured to display information related to infusion of fluid. The control unit may have a display that is larger, smaller or the same size as the pump module and, likewise, the user input mechanism (e.g. touch panel) of the control unit may be larger, smaller or the same size as the user input mechanism of the pump module. As the pump module is typically portable, and would generally have less display space and space for the user input mechanism, when coupled to the control unit, more detailed information regarding an infusion may be viewable.

It is desirable to take advantage of the capabilities of the control unit when the pump module is docked to the control unit. A smaller display on the pump module may be used to display information specific to an infusion running on the device when attached to the control unit. The full functionality of the user input mechanism on the pump module may be utilized when the pump module is detached from the control unit, such as in a transport mode.

In one aspect, there is disclosed a method of managing a modular infusion pump device, comprising: coupling a modular infusion pump to a control unit; establishing a data link between the modular infusion pump and control unit upon coupling the modular infusion pump to the control unit; transferring data between the modular infusion pump and the control unit as a result of the coupling control unit; and adjusting the behavior of the modular infusion pump and the control unit as a result of coupling the modular infusion pump to the control unit.

In another aspect, there is disclosed a patient care system, comprising: a control unit capable of coupling with multiple modular medical devices; and a modular medical device capable of being coupled with the control unit, wherein the behavior of the modular medical device automatically adjusts based on the status of being coupled or un-coupled with the control unit.

The details of one or more variations of the subject matter described herein are set forth in the accompanying drawings and the description below. Other features and advantages of the subject matter described herein will be apparent from the description and drawings, and from the claims.

DETAILED DESCRIPTION

Disclosed is a medical fluid infusion system configured for pumping a fluid to a patient, such as in a hospital environment. The system includes one or more modular infusion pump devices each of which is configured to be removably coupled to a control unit. The control unit and the one or more modular pump devices each include a display that is configured to display information. The information may be, for example, operating parameters of the pump device and alert indications and alarm messages although the information may vary widely. The control unit and the modular pump devices also each include one or more input mechanisms for initiating, modifying, or otherwise programing an infusion scenario for a patient.

As described in detail below, the infusion system is configured to modify the information that is displayed on the modular pump device and the control unit based on whether or not the modular pump device is docked or otherwise coupled to the control unit. The behavior of the control unit and the modular pump device may also be modified based on whether or not the modular pump device is docked or otherwise coupled to the control unit. For example, the responsibility for initiation or modification of infusion may be delegated to the control unit or to one or more of the modular pump devices. Or the responsibility may be allocated between two or more of the devices. This permits the user to take advantage of the varied capabilities of the control unit or a modular pump device in programming or initiating an infusion.

Figure 1A:
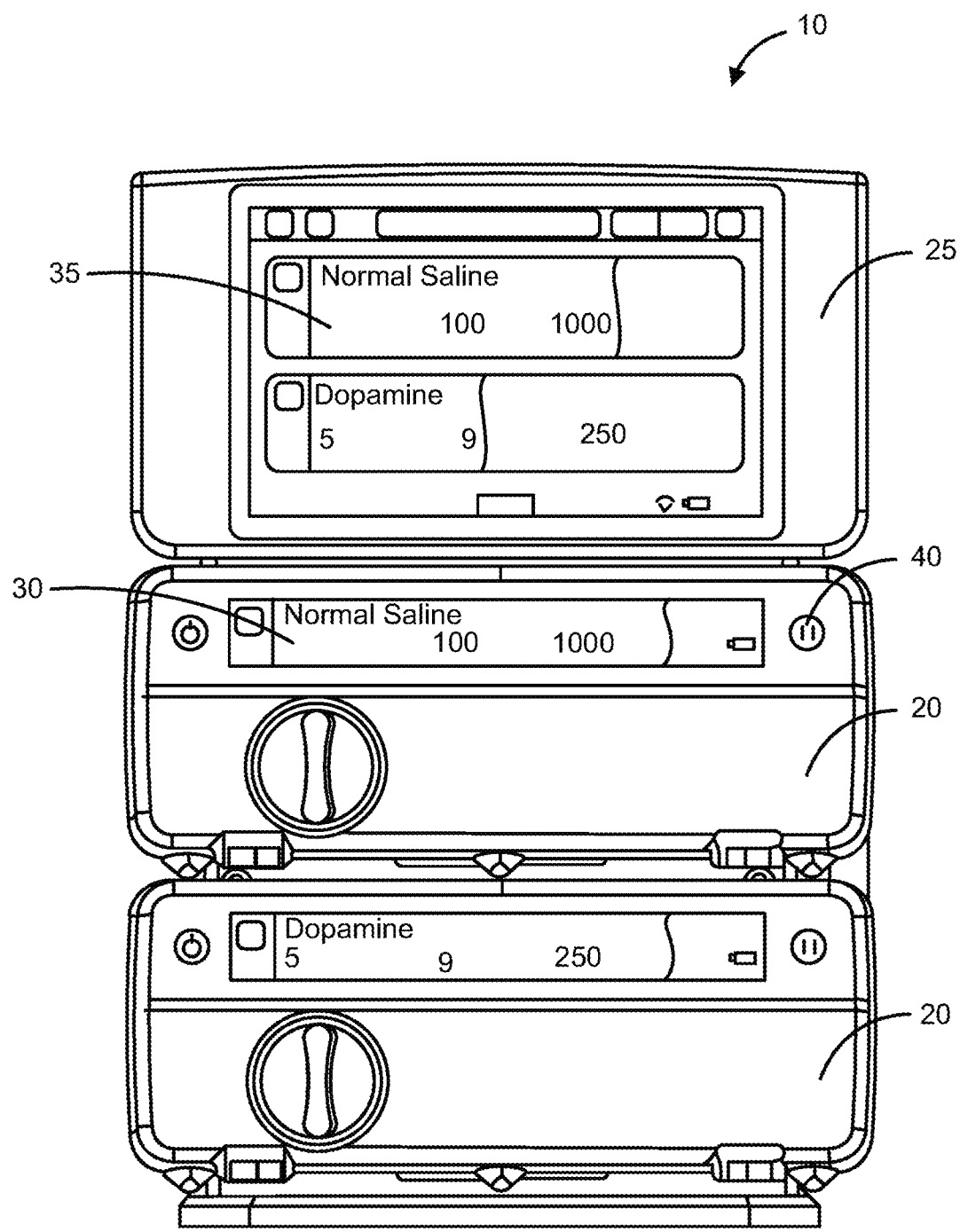
FIGS. 1A and 1B show front and side views, respectively, of a portion of a patient care system showing two fluid infusion pump modules mounted below a control unit, and the displays and control keys of each, with the control unit being capable of programming both infusion pumps.
Figure 1B:
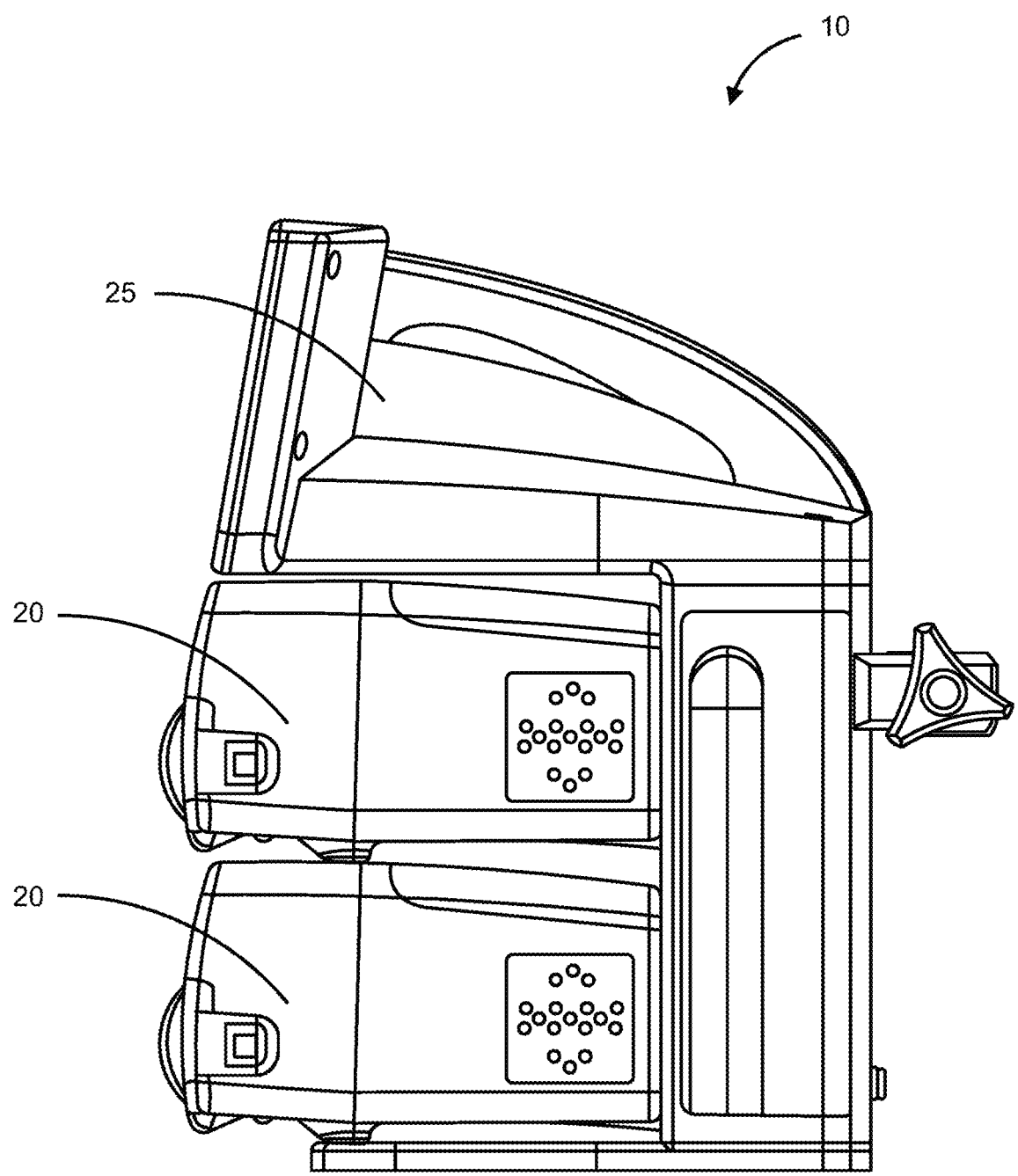

Referring now in more detail to the drawings in which like reference numerals refer to like or corresponding elements among the several views, there is shown in FIGS. 1A and 1B a patient care system 10 having modular infusion pumps 20. Each of the modular infusion pumps 20 mechanically, electrically and/or communicatively couples to a control unit 25, which is configured to provide control and/or monitoring capabilities for each of the one or more infusion pumps that are attached to it. The coupling between the infusion pumps and the control unit may vary and may be, for example, a mechanical or galvanic coupling or it may be a wireless, inductive or optical coupling. In any event, the control unit 25 and the respective infusion pumps are configured to detect when a coupling occurs and may modify the behavior of the respective devices accordingly, as described in detail below.

Fluid supplies may be attached or otherwise coupled to the system and may take various forms and may include bags, syringes or other types of containers. In certain embodiments, a single-channel infusion pump 20 is used to infuse each of the fluids of the fluid supplies into the patient. In other embodiments, a multi-channel infusion pump (such as the MedSystem® III Infusion Pump (CareFusion, San Diego, CA)) is used to infuse fluids into the patient. The infusion pumps are flow control devices that will act on a respective fluid line to move the fluid from the fluid supply through the fluid line to the patient. Each pump, or each channel within a pump, can be individually set to the pumping or operating parameters required for infusing the particular medical fluid from the respective fluid supply into the patient at the particular rate prescribed for that fluid by the physician. Such medical fluids may comprise drugs or nutrients or other fluids.

Referring to FIG. 1A, a view of the front of the infusion pumps 20 is shown. A display 30 such as an LCD display, is located in plain view on each of the infusion pumps 20 and may be used to visually communicate various information relevant to the pump, such as alert indications (e.g., alarm messages). The display 30 of the infusion pumps 20 may vary in size relative to the display 35 of the control unit 25. For example, the display 30 of the infusion pump 20 may often be smaller than the display 35 of the control unit 25 given that the infusion pumps are portable. The smaller display 30 may be lighter in weight than the display 35.

One or more control keys 40 and a user input mechanism (e.g. touch panel) may be included on the infusion pumps for programming and controlling operations of the infusion pump as desired. The infusion pumps 20 may also include audio alarm equipment in the form of a speaker 45, which, in certain embodiments, may only be used when the respective infusion pump is un-coupled from the control unit 25, while in transport mode.

In the embodiment shown, the control unit 25 is positioned above the attached infusion pumps 20. Other devices or modules, including another infusion pump, may be attached below the first modular infusion pump, as shown in FIGS. 1A and 1B. In such a system, each attached pump represents a pump channel of the overall patient care system 10. In an embodiment, the control unit 25 is used to provide an interface between the infusion pumps 20 and external devices as well as to provide most of the operator interface for the infusion pump 5. In other embodiments, the control unit 25 may be configured such that that infusion pump modules 25 are attached above, below or to the side of the control unit.

As mentioned, the control unit 25 includes a display 35 for visually communicating various information, such as the operating parameters of the infusion pumps 20 and alert indications and alarm messages. The control unit 25 may also include a speaker (not shown) to provide audible alarms. The control unit 25 or any other module also has various input devices in this embodiment, including control keys, touch panel, and a bar code or other scanner or reader for scanning information from an electronic data tag relating to the infusion, the patient, the care giver, or other. The control unit 25 may also have a communications system (not shown) which may communicate with external equipment such as a medical facility server or other computer and with a portable processor, such as a handheld portable digital assistant ("PDA"), or a tablet or laptop-type of computer, or other information device that a care giver may have to transfer information as well as to download drug libraries to a control unit or pump.

The communications system may take the form of a radio frequency ("RF") system, an optical system such as infrared, a Blue Tooth system, or other wired or wireless system. The bar code scanner and communications system may alternatively be included integrally with the infusion pump 20, such as in cases where a control unit is not used, or in addition to one with the control unit. Further, information input devices need not be hard-wired to medical instruments, information may be transferred through a wireless connection as well.

In some embodiments, the infusion pump module may also have a communication system that may take the form of a radio frequency ("RF") system, an optical system such as infrared, a Blue Tooth system, or other wired or wireless system.

FIGS. 1A and 1B show two infusion pumps 20 connected to the control unit 25. It should be appreciated that more (or less) infusion pumps may be connected to the control unit 25. Additionally, other types of modules may be connected to the control unit 25. Infusion pump modules types that are included within the scope of this disclosure include, but are not limited to Large Volume Parenteral 5 & 6, Syringe, Patient Controlled Analgesic ("PCA"), Enteral and Epidural modules. Additionally, patient monitoring modules may be attached physically and/or wirelessly to the control unit 25. The patient monitoring modules would be accessible and programmable by the control unit in the same fashion as the infusion pump modules.

Adjustment of User Interface Upon Coupling of Infusion Pump to Control Unit

As discussed, the infusion system 10 is configured to modify the information that is displayed on the infusion pump(s) 20 and the control unit 25 based on whether or not a modular infusion pump 20 is docked or otherwise coupled to the control unit 25. The infusion system may also initiate a transfer of data between one or more of the infusion pumps 20 and the control unit upon coupling of an infusion pump and the control unit 25. The data may vary and may include, for example, the patient's name, hospital identification number, and other information such as the patient's age, weight, condition, and allergies. The data may also include, for example, the patient's MAR (medication administration record), a drug identifier, a drug concentration, a diluent fluid identifier, a dose or flow rate, other pumping-related parameters, contra-indicated medications/conditions, alarm conditions, etc. Moreover, the system 10 may be configured to modify the type of data that is displayed or how the data is displayed (font size, color, brightness, etc.) between the displays of the control unit and infusion pumps as well as how notification of alarm conditions is handled.

Figure 2:
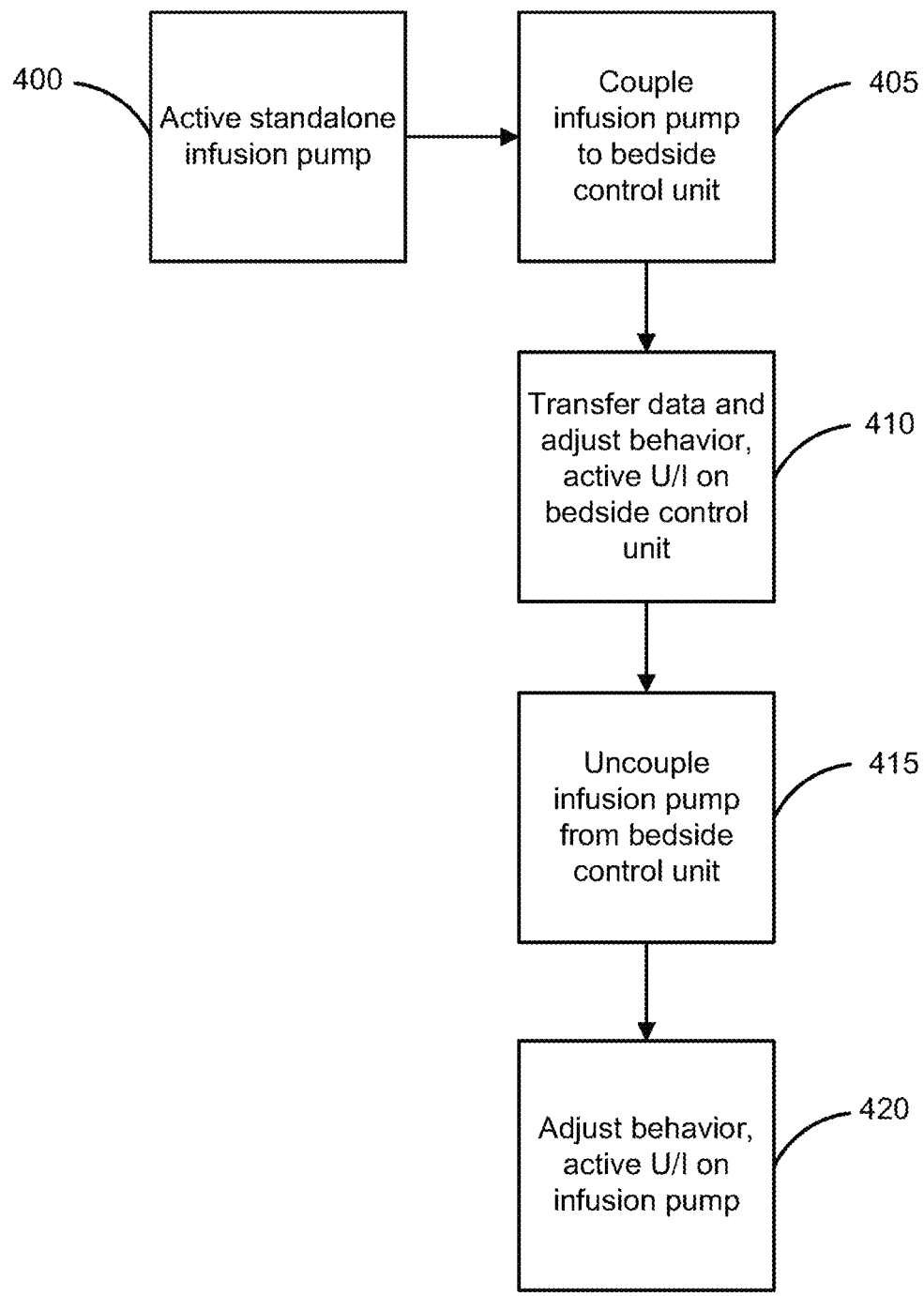
FIG. 2 diagrams the workflow of attaching and detaching a standalone pump module to a control unit as well as a transition of the user interface elements from one component to the next.

With reference to FIG. 2, there is now described a method of modifying the behavior of the modular infusion pump and the control unit based upon a whether or not the modular infusion pump and control unit are coupled to one another. In a first step 400, a practitioner activates a modular infusion pump in a standalone state. In such a standalone state, the infusion pump handles and manages the infusion of fluid to a patient. This includes keeping track of and displaying relevant data on its own display.

In step 405, a practitioner couples the modular infusion pump to the control unit. As mentioned, the coupling may be a direct or indirect mechanical coupling or it may be a wireless coupling. In this regard, a mechanical or wireless data link between the devices is established. In an embodiment, the modular infusion pump is attached or docked to a rack assembly that couples the modular infusion pump to the control unit. The modular infusion pump or the control unit may include a mechanical or software mechanism that triggers an alert upon the coupling event.

In a next step 410, a data transfer occurs between the modular infusion pump and the control unit. The type of data that is transferred may vary as discussed above. Data may be transferred from the modular infusion pump to the control unit, from the control unit to the modular infusion pump, or both. The data transfer may take advantage of increased computer memory capabilities between the devices, as well as variations in mechanical capabilities (such as speakers, display size, etc.) between the devices.

In an embodiment, the display of data, such as a user interface, is adjusted between the modular infusion pump and the control unit upon coupling of the modular infusion pump to the control unit. For example, the user interface of the control unit may be modified to display additional data related to the operation of the modular infusion pump whereas the user interface of the modular infusion pump is modified to display less data. The user interfaces of the respective devices may be modified in a variety of manners such as to share responsibility for displaying data related to the modular infusion pump. This can take advantage of the larger screen size, if present, of the control unit relative to the infusion pump. In an embodiment, certain components of the user interface remain with the modular infusion pump regardless of whether the modular infusion pump is coupled to the control unit. For example, the ability to pause infusion may remain with the controls of the modular infusion pump.

Alarm management features may also be modified between the modular infusion pump and the control unit upon coupling of the infusion module to a program module. For example, the control unit may take over responsibility for initiating audio or visual alarm signals from the modular infusion pump. In this regard, the control unit may receive alarm notifications from multiple modular infusion pumps that are attached to it. The control unit may rank or otherwise prioritize the multiple alarm signals and display or voice an alarm or alarms based on the rankings, such as an alarm that is deemed to be most important. The control unit may also take over responsibility for confirmation or acknowledgement of the alarm from the modular infusion pump. In such a situation, the clinician would acknowledge an alarm by interfacing with the control unit rather than with the modular infusion pump.

The responsibility for initiation or modification of infusion may also be modified between the modular infusion pump and the control unit upon coupling or uncoupling of the modular infusion pump to the control unit. Infusion programming or initiation responsibility may be delegated to the control unit or to one or more of the modular pump devices or it may be allocated between two or more of the devices. The user may then take advantage of the varied capabilities of the control unit or a modular pump device for programming an infusion. This may improve or augment the workflow efficiency during initiation of an infusion or entry of infusion parameters. For example, the user may take advantage of the possibly larger display and/or richer interactivity capabilities of the control unit versus the modular infusion pump. The larger display unit and/or input mechanisms on the control unit may also allow the use of more complex protocols that might be impractical or inconvenient on the smaller landscape of the modular infusion pump.

With reference again to FIG. 2, in a next step 415, the modular infusion pump is decoupled from the control unit. As discussed, the modular infusion pump or the control unit may include a mechanical or software mechanism that triggers an alert upon the coupling event or decoupling event. The method then proceeds to step 420, where the device again initiate a data transfer and re-allocation of duties. For example, the control unit will revert responsibility for display of data and alarm management to the modular infusion pump.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a device having a display device, such as for example a liquid crystal display (LCD) monitor for displaying information to the user and a keyboard and a input device, such as for example a mouse or a trackball, by which the user may provide input to the device. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) when depicted in the accompanying figures and/or described herein do not necessarily require the particular order shown, or sequential order, to achieve desirable results. Other implementations may be within the scope of the following claims.

The invention claimed is:

1. A pump system, comprising:
a modular infusion pump having a microprocessor, wherein the modular infusion pump couples to a patient via a fluid line, wherein the modular infusion pump couples to a control unit and wherein data is transferred between the modular infusion pump and the control unit when the modular infusion pump and the control unit are coupled to one another, wherein the microprocessor is configured to:
detect that the modular infusion pump has been coupled to or uncoupled from the control unit;
cause the modular infusion pump to automatically undergo an adjustment in behavior based on the status of being coupled to or un-coupled from the control unit and wherein the behavior of the modular infusion pump adjusts differently depending on whether the infusion modular pump is coupled to the control unit wirelessly, electrically or mechanically, and wherein the adjustment in behavior comprises a modification of a user interface of the modular infusion pump and wherein the modification of the user interface relates to an aspect of the user interface that enables a user to actively control an initiation or modification of an infusion by the modular infusion pump.

2. The pump system of claim 1, wherein the modular infusion pump has a first display and the control unit has a second display.

3. The pump system of claim 2, wherein the first display and the second display are different sizes.

4. The pump system of claim 1, wherein data is transferred from the modular infusion pump to the control unit when the modular infusion pump and the control unit are coupled to one another.

5. The pump system of claim 1, wherein data is transferred from the control unit to the modular infusion pump when the modular infusion pump and the control unit are coupled to one another.

6. The pump system of claim 1, wherein the data includes infusion program data.

7. The pump system of claim 1, further comprising the control unit.

8. A non-transitory computer readable medium comprising instructions executable by a processor to cause a modular infusion pump of a medical fluid delivery system to:
detect that the modular infusion pump has been coupled to or uncoupled from a control unit;
cause the modular infusion pump to automatically undergo an adjustment in behavior based on the status of being coupled to or un-coupled from the control unit and wherein the behavior of the modular infusion pump adjusts differently depending on whether the infusion modular pump is coupled to the control unit wirelessly, electrically or mechanically, and wherein the adjustment in behavior comprises a modification of a user interface of the modular infusion pump and wherein the modification of the user interface relates to an aspect of the user interface that enables a user to actively control an initiation or modification of an infusion by the modular infusion pump.

9. The non-transitory computer readable medium of claim 8, wherein the modular infusion pump has a first display and the control unit has a second display.

10. The non-transitory computer readable medium of claim 9, wherein the first display and the second display are different sizes.

11. The non-transitory computer readable medium of claim 8, wherein data is transferred from the modular infusion pump to the control unit when the modular infusion pump and the control unit are coupled to one another.

12. The non-transitory computer readable medium of claim 8, wherein data is transferred from the control unit to the modular infusion pump when the modular infusion pump and the control unit are coupled to one another.

13. The non-transitory computer readable medium of claim 8, wherein the data includes infusion program data.

14. The non-transitory computer readable medium of claim 8, wherein a user input mechanism on the modular infusion pump is disabled upon coupling with the control unit.

15. The non-transitory computer readable medium of claim 8, wherein the adjustment in behavior further comprises an allocation of alarm management duties between the control unit and the modular infusion pump.

16. The non-transitory computer readable medium of claim 8, wherein the adjustment in behavior further comprises assigning responsibility for issuing alarm notifications to the control unit.

17. The non-transitory computer readable medium of claim 8, wherein the adjustment in behavior further comprises assigning responsibility for acknowledging alarm notifications to the control unit.

18. The non-transitory computer readable medium of claim 8, wherein the adjustment in behavior further comprises assigning responsibility for infusion programming for the coupled modular infusion pump to the control unit.

19. The non-transitory computer readable medium of claim 8, wherein the adjustment in behavior further comprises switching from a battery-powered mode to a recharging mode when the modular infusion pump is in electrical communication with the control unit.

20. The non-transitory computer readable medium of claim 8, wherein the adjustment in behavior further comprises allocating responsibility for programming of infusion parameters between the modular infusion pump and the control unit.

21. The pump system of claim 1, wherein the modification of the user interface relates to a reallocation of the user interface based on a size of the user interface.

22. The pump system of claim 21, wherein the modification of the user interface relates to a reallocation of the user interface based on the size of the user interface of the modular infusion pump taking into account a size of a second user interface of the control unit.

\* \* \* \* \*